United States Patent [19]

Deryabin

[11] Patent Number: 5,061,491

[45] Date of Patent: Oct. 29, 1991

[54] MEDICINAL AGENT AND METHOD FOR TREATMENT OF MASTITIS IN ANIMALS AND HUMANS

[76] Inventor: Alexandr M. Deryabin, pereulok N. Ostrovskogo, 12, kv. 5, Moscow, U.S.S.R.

[21] Appl. No.: 384,175

[22] Filed: Jul. 21, 1989

[30] Foreign Application Priority Data

Dec. 30, 1988 [SU] U.S.S.R. ............................. 4627363

[51] Int. Cl.$^5$ .............................................. A61K 35/78
[52] U.S. Cl. .................................. 424/195.1; 514/886; 514/887
[58] Field of Search ..................... 424/195.1; 514/886, 514/887

[56] References Cited

U.S. PATENT DOCUMENTS 4,839,171  6/1989  Nelson ......................... 424/195.1 X

OTHER PUBLICATIONS

Lust, *The Herb Book*, First Edition, pp. 94–97, 138–141, 156–157, 166–167, 180–181, 194–197, 206–207, 260–261, 268–271, 284–285, 304–307, 332–333, 368–369, 382–383 (1974).

Steinmetz, *Codex Vegetabilis*, Ref. Nos. 192–195, 841–846 (1957).

Kloss, *Back to Eden*, pp. 178–179, 298–299, 316–317, 450–451 (1949).

*Primary Examiner*—John W. Rollins
*Attorney, Agent, or Firm*—Burgess, Ryan & Wayne

[57] ABSTRACT

A medicinal agent for treatment of mastitis in animals and humans which includes a mixture of a decoction of a mixture of the following medicinal herbs in equal parts by weight and an ammonia solution infusion which is a mixture of the same medicinal herbs in equal parts by weight, wherein the medicinal herbs include *Matricaria chamomilla* L., flores *Calendulae officinalis* L., *Urtica dioica* L., *Erythreae centaurium* Raf. L., gemmae *Betula pendula* Roth, *Plantago major* L., gammae *Pinus sylvestris* L., *Origanum vulgare* L., *Salvia officinalis* Hoffm., *Archangelica officinalis* Hoffm., *Taraxacum officinale* Web., folium *Tussilaginis farfarae* L., *Sanguisorba officinalis* L., *Valeriana officinalis* L., *Menthae piperitae* L., *Thymus vulgaris* L., and *Bidens tripartita* L. The decoction and infusion are mixed in a ratio to adjust the Ph of the mixture to not below 7.4. Also disclosed is a method of treating mastitis using the medicinal agent described above.

7 Claims, No Drawings

MEDICINAL AGENT AND METHOD FOR TREATMENT OF MASTITIS IN ANIMALS AND HUMANS

FIELD OF THE INVENTION

The present invention relates to veterinary medicine and has particular reference to a novel medicinal agent for treatment of mastitis in animals and humans, and to a method for treatment of the disease.

The proposed agent is applicable in veterinary medicine for treatment of various kinds of mastitis in animals of all species, as well as in medical practice for treatment of mastitis in humans.

BACKGROUND OF THE INVENTION

At present chemotherapeutic agents are widely used for treatment of mastitis in animals and humans, antibiotics, penicillin and streptomycin being the most commonly applied drugs (81 percent).

A variety of medicinal compositions are currently known for treatment of mastitis in animals, the compositions being based on antibiotics and incorporating an oleaginous base, prednisolone, a foaming agent, and a propellant. However, application of said agents is inadequately efficient. Treatment of mastitis with antibiotics-based drugs is causative of side effects and gastrointestinal disorders, and affects an organism's resistive power. Besides, meat and milk of affected animals contain residual quantities of medicinal substances used in treatment of mastitis.

Known in the modern medical practice is the use, as an agent for treatment of mastitis, of ichthammol (an ammonium salt of sulfo acids of shale oil) (cf. Medicinal agents and biopreparations in fur breeding, A Handbook, by F. G. Nabiyev, A. A. Dragunov, and R. G. Rakhmatullin. 1986, Agropromizdat Publishers, Moscow, pp. 110–111; Medicinal agents in veterinary medicine, by D. K. Cherviakov, P. D. Yevdokimov, and A. S. Vishker, 1970, Kolos Publishers, Moscow, p. 300 (in Russian).

Ichthammol features an antimicrobial, antipyretic, locally anesthetic and keratolytic action, its main active principles being sulfur and some aromatic substances. The drug is applied as a 10- to 30-percent ointment or 10- to 20-percent alcoholic solutions. Ichthammol ointment is applied to the animal's udder affected by mastitis, along with fats or in a glycerol solution. However, ichthammol ointment is a low-efficacious drug, since it is poorly absorbable by the tissue being treated the ointment is hard to penetrate into tissue especially its deeply seated layers. The ointment is most commonly applied in combination with some other therapeutic substances.

SUMMARY OF THE INVENTION

The proposed medicinal substance and the treatment method are novel and have not to date been described in literature.

It is a primary object of the present invention to provide a novel medicinal agent featuring high therapeutic efficacy in treatment of mastitis, which is nontoxic and free from any side effects.

It is another object of the present invention to provide a method for treatment of mastitis, featured by high efficiency and simple in implementation.

These primary and further objects are accomplished by providing a medicinal agent for treatment of mastitis in animals and humans, said medicinal, according to the invention, comprises a mixture of a decoction and an ammonia-solution infusion of the following medicinal herbs taken in equal parts by weight:

wild camomile,
pot marigold (flowers),
stringing nettle,
common centaury,
pine buds,
common plantain,
birch buds,
pot marjoram,
garden sage,
garden angelica,
dandelion,
coltsfoot (leaves),
great burnet,
common valerian,
peppermint,
common thyme,
tripartite bur-marigold;

said decoction and said infusion being taken in a ratio giving the pH value of the mixture not below 7.4.

The proposed agent contains preferably an infusion of said herbs in a 25-percent aqueous ammonia solution.

The proposed medicinal agent features preferably the following volume percent ratios of the original components:

a decoction of said herbs, 70 to 80;
an infusion of said herbs, 30 to 20.

The proposed agent may contain additionally a mixture of a decoction and an infusion of the following herbs taken in equal parts by weight: small-leaved lime (flowers), bog cudweed, motherwort, common immortelle, celandine poppy, southern blue gum-tree, milfoil (flowers), common Saint-John's-wort, senna leaves, fennel (seeds).

The proposed medicinal agent for treatment of mastitis is highly effective, its application resulting in 98 to 100-percent recovery.

Application of the proposed agent improves organoleptic properties of milk and destroys its pathogenic flora in convalescent animals, as well as contributes to prompt tissue regeneration in cases of injuries.

Unlike treatment with antibiotics, followed as a rule by partial atrophy of the mammary gland and its reduced function, treatment with the proposed agent results in enhanced function of the mammary gland and hence an increased amount and a better quality of milk given.

Application of the proposed agent for treatment of mastitis in cows is conducive to a fast restoration of milk-yield at dairies.

The present invention covers also methods for treatment of mastitis in animals and humans, involving application of the proposed medicinal agent.

A method for treatment of mastitis in animals, according to the invention, consists of applying the medicinal agent to the inflamed area of the udder, the teats exclusive, whereupon with a view to enhancing lactation, said inflamed area is subjected to light massage for 5 to 7 minutes till said area turns pink; said procedure is repeated twice or thrice a day, a treatment course taking 3 to 15 days.

It is expedient when treating mastitis in cows, that application of the proposed medicinal agent to the inflamed area be preceded by milking of the affected animal and that intense milking be carried out in the course of said massage procedure.

A method for treatment of mastitis in females, according to the invention, consists in that, having withdrawn milk from the mammary gland, the proposed medicinal agent is applied to the inflammation-affected breast area until the latter turns pink or a light tingling sensation appears in said area; the aforesaid procedure is repeated two or three times a day, a treatment course lasting 3 to 15 days till complete convalescence of the patient.

DETAILED DESCRIPTION OF THE INVENTION

The proposed medicinal agent is in fact a mixture of a decoction and an ammonia-solution infusion of a number of medicinal herbs, said decoction and said infusion being taken in a ratio that provides for the pH value of said mixture not below 7.4.

The following herbs are used as said medicinal herbs for preparation of the aforesaid decoction and infusion: wild camomile (*Matricaria chamomilla* L.), pot marigold (flowers) (*Calendula officinalis* L.), stinging nettle (*Urtica dioica* L.), common centaury (*Erythreae centaurium* Raf. L.), pine buds (Gemmae Pini), common plantain (*Plantago major* L.), birch buds (Gemmae Betulae), pot marjoram (*Origanum vulgare* L.), garden sage (*Salvia officinalis* L.), garden angelica (*Archangelica officinalis* Hoffm.), dandelion (*Taraxacum officinalis* Web.), coltsfoot (leaves) (*Tussilago farfara* L.), great burnet (*Sanguisorba officinalis* L.), common valerian (*Valeriana officinalis* L.), peppermint (*Menthae piperitae* L.), common thyme (*Thymus vulgaris* L.), tripartite bur-marigold (*Bidens tripartita* L.).

The set of medicinal herbs is indispensable for preparation of the proposed agent. To attain more efficient action of the proposed agent, the following herbs are added to the aforesaid set of medicinal herbs: small-leaved lime (floweres) (*Tilia cordata* Nill.), bog cudweed (*Gnaphalium uliginosum* L.), motherwort (*Lenourus cardiaca* L.), common immortelle (*Helichrysum arenarium* Moench), celandine poppy (*Chelidonum majus* L.), southern blue gum-tree (*Eucalyptus globulus* Labill.), milfoil (flowers) (*Achillea millefolium* L.), common Saint-John's-wort (*Hypericum perforatum* L.), senna leaves (folium Cassia, *Cassia acutifolia* Del.), fennel (seeds) (*Foeniculum vulgare* Mill.). To prepare a decoction and an infusion from said herbs one must proceed as follows:

A mixture of the aforelisted herbs taken in equal parts by weight is poured with boiling water (three liters per 100 to 130 g of said mixture of the medicinal herbs). In 7 to 8 hours the mixture is subjected to straining. To prepare an infusion, a mixture of the aforementioned herbs taken in equal weight parts, is poured with ammonia solution (preferably a 25-percent aqueous solution), taken an amount of three liters of such an aqueous ammonia solution per 100 to 130 g of said mixture of the medicinal herbs. The mixture is allowed to infuse for 7 to 10 days and then is subjected to straining. The preprepared decoction and infusion are mixed in such a ratio that the pH of the resultant mixture be not below 7.4. It is expedient to intermix the decoction and infusion in the following ratio (vol. %):
decoction, 70 to 80;
infusion, 30 to 20.

The finished product thus obtained is essentially a liquid colored dark cherry-red, having an odor of ammonia and of medicinal herbs.

The proposed agent contains a great deal of diverse biologically potent substances said plants incorporate, such as alkaloids, glycosides, tanning agents, saponins, flavonoids, various organic acids, vitamins, glyceride and essential oils, microelements, and others. All said substances, while acting on a living organism integrally cause a physiological effect even when applied in very low amounts. The proposed agent has been evaluated experimentally on test animals and clinically on patients.

A biological effect of the proposed agent has been studied on laboratory animals.

In experiments performed test rats having a mass of 210 to 230 g, were given the proposed agent externally by applying it to the skin as a strip 20 mm wide and 100 to 110 mm long, running along the spine, in a dose of 10 ml for a first group of the animals, 20 ml for a second group of the animals, and 30 ml for a third group of the animals. The application of the proposed agent was repeated many times until the agent dried completely on the area mentioned above. Repeated application of the proposed agent to the test animals' skin was carried out at 55 to 60-minute intervals for six hours. The test rats were followed-up for 5 days.

The studies performed demonstrated that the animals to which the proposed agent was applied within the initial two or three minutes of the experiment, exhibited unrest, which was expressed in active movement of the animals over the cage attempts to get rid of the agent by shaking the hair-covering. In all test animals the skin at the area of application of the proposed agent was slightly hyperemic, while skin hyperemia disappeared in 6 to 8 hours after the last application procedure. It was eastablished by morphological and biochemical blood examinations that the concentration of erhthrocytes and hemoglobin in the blood of the experimental rats increased by 2.4 to 3.9 and 3.3 to 6.8 percent, respectively, while the blood sugar content increased by 3.7 to 9.3 percent ($P>0.05$), the lysozyme activity, by 10.1 to 12.6 percent ($P<0.05$), and the glycogen and ascorbic acid content of the liver, by 13.3 to 14.3 percent, respectively.

No changes in the test animals' behaviour were found within the follow-up period; the animals took food and water unobstructedly, they were mobile, no mortality cases occurred in that period of time.

The examinations performed have demonstrated that the proposed agent is not toxic for animals when applied to the skin.

The proposed agent has been tested on diverse farm animals for treatment of various-etiology mastitis, i.e., serous mastitis, catarrhal, fibrous, and suppurative-catarrhal mastitis.

The proposed agent was applied to the inflamed area, the teats exclusive. Then light massage carried out on the affected area for 5 to 7 minutes until the skin of said area turns pink. The procedure mentioned above was repeated two or three times a day after milking the affected animal dry. Milking was carried out in the course of massage as well. As a result of application of the proposed agent the wounds became free of purulent-necrotic debris, whereupon the wounds healed and edema disappeared in 2 to 5 days. A treatment course lasted from 3 to 15 days depending on the degree of severity of the disease. A control examination carried out in 15 days demonstrated complete destruction of pathogenic microflora in milk and restoration of the milk-yield of the affected animals.

The proposed medicinal agent was also evaluated clinically on human patients suffering from the following diseases: purulent mastitis, and serous mastitis. The proposed agent was applied to the inflamed area, the nipples exclusive until the skin of that area turned pink or a light tingling sensation appeared in said area. The procedure was repeated two or three times a day, having withdrawn milk from the mammary gland before application of the proposed agent. The patients thus treated felt amelioration within the first days of said procedure, the body temperature normalized, painful sensations alleviated. In the following days painful sensations disappeared completely, mammary engorgement ceased, induration resorbed. The treatment course lasted 3 to 15 days till complete recovery of the patients.

The proposed agent caused neither complications nor side effects, nor features said agent any contraindications for use.

To promote understanding of the present invention given below are some specific examples of practical trails of the proposed agent.

EXAMPLE 1

A total of 45 cows affected by mastitis of a different degree of severity were treated with the proposed agent.

As a result of clinical examination of the animals' udder it was found that the diseased animals suffered from the following forms of mastitis:
serous and catarrhal—20 heads,
fibrous—16 heads,
suppurative-catarrhal—9 heads.

Treatment of 16 cows affected by the fibrous form and of 9 animals with suppurative-catarrhal mastitis, using conventional therapy failed to provide positive results.

The proposed agent was applied to the udder skin of the affected animals after each milking, whereupon light massage was done for 5 to 7 minutes three times a day.

As a result of the treatment performed all the 20 animals of the first group (suffering from serous and catarrhal mastitis) recovered on the 2th or 5th day, accompanied by complete restoration of the milk-yield.

The animals of the second group with fibrous mastitis (16 heads) recovered on the 8th or 10th day of treatment and their milk-yield restored gradually.

7 animals of the third group suffering from suppurative-catarrhal mastitis, were treated for 15 days, whereupon they were considered clinically sound.

In two cows with the severest chronic form of suppurative-catarrhal mastitis and atrophy of the teats the inflammatory process was arrested by 30th day of treatment, whereupon milk secretion appeared. However, milk-yield of those cows was not restored completely. Thus, of 45 diseased animals subjected to treatment with the proposed agent 43 cows were cured completely and returned to a milk-producing group.

EXAMPLE 2

Four cows affected with following forms of the diseases were treated with the proposed agent: serous mastitis of the right anterior lobe; fibrous mastitis of the left anterior and posterior lobes; fibrous mastitis of the left posterior lobe, accompanied by massive induration; serous mastitis of the left anterior and the right anterior lobes, accompanied by bad edema of the udder.

The proposed agent was applied to the affected area and light rubless massage was carried for 5 to 7 minutes, the specific consumption of the agent being 100 ml per animal. The agent was applied three times a day after the cows had been milked dry. The treatment was carried out by the open method, without bandages or dressings. No changes in the routine upkeep and feed ration of the animals were made.

The treatment process of individual animals proceeded as follows.

The first cow with the diagnosis of serous mastitis of the right anterior lobe.

Treatment with the proposed agent started in four days after the onset of the disease. The agent was applied to the affected area three times daily after milking. Painful sensations and induration of the udder lobe reduced considerably on the second day of treatment, complete recovery occurred on the third day.

The second cow with the diagnosis of fibrous mastitis of the left anterior and posterior lobes.

Treatment with the proposed agent began on the third day after the onset of the disease. On the second day of treatment with the proposed agent the cow became quiet, the left anterior lobe got soft, while induration in the left anterior lobe persisted but became soft and reduced in size twofold. After a three-day treatment course the cow was considered sound.

The third cow with the diagnosis of fibrous mastitis of the left posterior lobe, massive induration on the left side.

Treatment started in three days after the disease had been revealed. After two days of treatment with the proposed agent the cow became quiet the induration got soft and reduced in size considerably. After a four-day treatment course the induration disappeared fully.

The fourth cow with the diagnosis: serous mastitis of the left anterior and the right anterior lobes, accompanied bad edema of the udder, considerable painfulness and sanious discharge from the affected udder lobes. The cow was unrest and was not amenable to milking.

After a three-day treatment course with the proposed agent the udder became soft, the tumor decreased, the sanious discharge ceased. The cow became quiet and was amenable to milking well.

EXAMPLE 3

A total of 48 cows affected with chronic forms of mastitis were taken from a herd of dairy cows made up of 800 heads for evaluating the proposed medicinal agent.

Clinical examination established that the diseased animals suffered from the following forms of mastitis:
serous—4 heads
serous-catarrhal—18 heads
catarrhal—21 heads
fibrous—1 head
suppurative-catarrhal—3 heads
hemorrhagic—1 head.

Treatment of 28 animals by conventional methods failed to provide positive results.

The proposed agent was applied to the affected area and the latter was subjected to light massage for 5 to 7 minutes. The preparation was applied three times a day after the cows had been stripped of milk. No changes in the routine upkeep and feed ration of the animals were made. The treatment course lasted 9 days. As a result of the treatment all the 48 cows were considered sound.

EXAMPLE 4

A total of 31 animals affected the various forms of mastitis were taken out of a herd of 967 dairy cows.

Clinical examination revealed that the diseased animals suffered from the following forms of mastitis:
serous and catarrhal—8 heads
fibrous—7 heads
suppurative-catarrhal—16 heads.

Treatment of 7 animals with fibrous mastitis and 16 animals with suppurative-catarrhal mastitis failed to give positive results.

The proposed agent was applied to the affected area in each of the diseased animals after each milking, followed by light massage for 5 to 7 minutes three times a day.

As a result of the treatment given to the animals of the first group (serous and catarrhal mastitis), the affected animals recovered on the 3rd or 6th day and was accompanied by restoration of the milk-yield, whereas three cows with the severest form of mastitis were treated further on.

Thus, 28 animals out of 31 subjected to treatment with the proposed agent, were cured and returned to a milk-producing group.

EXAMPLE 5

A total of 64 cows affected by the various forms of mastitis were taken out of a herd of dairy cows. It was established after a clinical examination that the diseased animals suffered from the following forms of mastitis:
catarrhal—39
fibrous—9
suppurative-catarrhal—16.

Treatment of 18 diseased animals using conventional methods failed to provide positive results.

The treatment course lasted 13 days on the average.

The proposed agent was applied to the affected area after the cows had been milked dry, whereupon light massage was carried out of said area for 5 to 7 minutes until the latter turned pink.

As a result of the treatment performed 63 out of 64 treated cows exhibited complete recovery.

EXAMPLE 6

A total of 30 cows affected by mastitis were subdivided into two groups 16 cows of the test group were treated with the proposed agent, whereas 14 animals of the control group were given antibiotics.

One of the cows in the control group was sent to a packing house on account of its too low milk-yield.

The test data obtained are tabulated in the table below

| Group of cows | Diagnosis | Number of cows | Duration of treatments (days) | Number of cows treated recovered | improved state | non-recovered |
|---|---|---|---|---|---|---|
| Test | Catarrhal mastitis | 9 | 2 | 9 | — | — |
| | Serous mastitis | 3 | 5.3 | 3 | — | — |
| | Serous-catarrhal mastitis | 4 | 7 | 3 | 1 | — |
| Control | Catarrhal mastitis | 7 | 7 | 3 | 3 | 1 |

-continued

| Group of cows | Diagnosis | Number of cows | Duration of treatments (days) | Number of cows treated recovered | improved state | non-recovered |
|---|---|---|---|---|---|---|
| | Serous-catarrhal mastitis | 6 | 6 | 2 | 2 | 2 |

What we claim is:

1. A medicinal agent for treatment of mastitis in animals and humans, comprising a mixture of a decoction consisting of a mixture of the following medicinal herbs in equal parts by weight and an ammonia solution infusion consisting of a mixture of the following medicinal herbs in equal parts by weight:
   Matricaria chamomilla L.,
   flores Calendulae officinalis L.,
   Urtica dioica L.,
   Erythreae centaurium Raf. L.,
   gemmae Betula pendula Roth,
   Plantago major L.,
   gemmae Pinus sylvestris L.,
   Origanum vulgare L.,
   Salvia officinalis Hoffm.,
   Archangelica officinalis Hoffm.,
   Taraxacum officinale Web.,
   folium Tussilaginis farfarae L.,
   Sanguisorba officinalis L.,
   Valeriana officinalis L.,
   Menthae piperitae L.,
   Thymus vulgaris L., and
   Bidens tripartita L.;
said decoction and infusion being mixed in a ratio to adjust the pH of the mixture to not below 7.4.

2. A medicinal agent as claimed in claim 1, wherein said mixture consists of the following volume percent ratios:
   a decoction of said herbs 70 to 80,
   an infusion of said herbs 30 to 20.

3. A medicinal agent as claimed in claim 1, further comprising an additional mixture of a decoction consisting of a mixture of the following medicinal herbs in equal parts by weight and an infusion consisting of the following medicinal herbs in equal parts by weight:
   flores Tiliae cordatae Nill,
   Gnaphalium uliginosum L.,
   Leonurus cardiaca L.,
   Helichryzum arenarium Moench.,
   Chelidonium majus L.,
   Eucalyptus globulus Labill.,
   flores Schilleae millefolii L.,
   Hypericum perforatum L.,
   folium Cassiae acutifoliae Del., and
   fructus Foeniculi vulgare Mill.

4. A medicinal agent as claimed in claim 1, wherein said ammonia solution infusion is an aqueous ammonia solution containing 25% by weight of ammonia based on three liters of said aqueous ammonia solution per 100 to 130 grams of said medicinal herbs in said infusion mixture.

5. A method for treatment of mastitis in animals, which comprises applying the agent of claim 1 to the inflamed area of the udder, whereupon for the sake of better lactation, said inflamed area is subjected to light massage for 5 to 7 minutes until said area turns pink; said procedure is repeated two or three times a day, a treatment course lasting 3 to 15 days.

6. A method for treatment of mastitis in cows, as claimed in claim 5, wherein application of the medicinal agent to the inflamed area is preceded by milking the cow dry, thereafter applying said medicinal agent to the inflamed area, and subjecting said inflamed area to light massage while attempting to milk said cow.

7. A method for treatment of mastitis in human females, comprises withdrawing milk from the mammary gland, and applying the medicinal agent as claimed in claim 1 to the inflamed area until said area turns pink or a light tingling sensation appears therein; said procedure is repeated two or three times a day, a treatment course lasting 3 to 15 days until complete convalescence occurs.

* * * * *